United States Patent [19]

Choy et al.

[11] Patent Number: 5,670,517
[45] Date of Patent: Sep. 23, 1997

[54] IRREVERSIBLE HIV PROTEASE INHIBITORS, COMPOSITIONS CONTAINING SAME AND PROCESS FOR THE PREPARATION THEREOF

[75] Inventors: Nakyen Choy; Hoil Choi; Chi-Hyo Park; Young-Chan Son; Chang-Sun Lee; Heungsik Yoon; Sung-Chun Kim; Jong-Sung Koh; Chung-Ryeol Kim, all of Daejeon, Rep. of Korea

[73] Assignee: LG Chemical Limited, Seoul, Rep. of Korea

[21] Appl. No.: 659,791

[22] Filed: Jun. 6, 1996

Related U.S. Application Data

[63] Continuation-in-part of Ser. No. 341,352, Nov. 17, 1994, which is a continuation-in-part of Ser. No. 159,382, Nov. 30, 1993, Pat. No. 5,587,388.

[30] Foreign Application Priority Data

Dec. 8, 1994 [KR] Rep. of Korea .................. 92-33272

[51] Int. Cl.[6] .................. A61K 31/47; A61K 31/335; C07D 217/15; C07D 215/14
[52] U.S. Cl. .................. 514/307; 514/314; 514/475; 546/146; 546/169; 549/552
[58] Field of Search .................. 546/146, 169; 549/552; 514/307, 314, 475

[56] References Cited

U.S. PATENT DOCUMENTS

| | | | |
|---|---|---|---|
| 5,545,750 | 8/1996 | Kempf et al. .................. | 564/360 |
| 5,587,388 | 12/1996 | Kim et al. .................. | 514/314 |

*Primary Examiner*—José G. Dees
*Assistant Examiner*—Mary C. Cebulak
*Attorney, Agent, or Firm*—Anderson Kill & Olick, P.C.

[57] ABSTRACT

The present invention relates to novel compounds of formula (I) which has inhibitory activities against human immunodeficiency virus ("HIV") protease, a process for the preparation thereof, and compositions for prevention or treatment of AIDS by HIV infection comprising the above compounds as active ingredients.

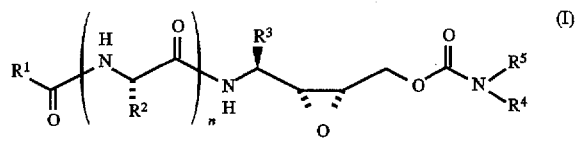

wherein:

$R^1$ is an aromatic group, a nitrogen-containing aromatic group, $C_{1-4}$ alkyl group optionally substituted with an aromatic group or a nitrogen-containing aromatic group, $C_{1-4}$ alkoxy group optionally substituted with an aromatic group or a nitrogen-containing aromatic group;

$R^2$ is an amino acid residue or a $C_{1-8}$ alkyl group substituted with a $C_{1-4}$ alkylsulfonyl group;

$R^3$ is a $C_{1-4}$ alkyl group optionally substituted with an aromatic group;

$R^4$ is hydrogen or a $C_{1-2}$ alkyl group;

$R^5$ is a $C_{1-10}$ alkyl group optionally substituted with an aromatic group; and n is 1 or 2.

8 Claims, No Drawings

IRREVERSIBLE HIV PROTEASE INHIBITORS, COMPOSITIONS CONTAINING SAME AND PROCESS FOR THE PREPARATION THEREOF

CROSS REFERENCE TO RELATED APPLICATION

This application is a continuation-in-part application of copending U.S. Ser. No. 08/341,352 filed on Nov. 17, 1994, which is a continuation-in-part application of copending U.S. Ser. No. 08/159,382 filed on Nov. 30, 1993, now U.S. Pat. No. 5,587,388.

FIELD OF THE INVENTION

The present invention relates to novel compounds for inhibiting human immunodeficiency virus ("HIV") protease and pharmaceutical compositions for the prevention or treatment of AIDS(acquired immuno-deficiency syndrome) caused by HIV infection containing the compounds as active ingredients.

BACKGROUND OF THE INVENTION

HIV-1 which is known to cause AIDS(acquired immunodeficiency syndrome) is one of retroviruses which contain their genetic information in RNA; and consists of a core, envelope proteins and a lipid membrane. The HIV core comprising two single-stranded RNA and reverse transcriptase is enclosed by envelope proteins, which are in turn enclosed by a lipid membrane.

The reverse transcriptase makes double-stranded DNA from a single-stranded RNA template and, consequently, only retroviruses, i.e., RNA viruses, have a reverse transcriptase. When retroviruses infect a host, the reverse transcriptase makes double-stranded DNA from a single-stranded virus RNA template. The resulting virus DNA is grafted into the host chromosome by integrase, and the transformed host makes new virus RNA's as well as virus proteins by using the host enzyme mechanism. The proteins thus produced are modified by host or virus enzymes to form new viruses. One important enzyme among the protein-modifying enzymes mentioned above is protease, which proteolyzes polyproteins into structural proteins and enzymes required for the virus replication.

Among the proteases of retroviruses, HIV protease has been studied most extensively. As mentioned above, HIV does not synthesize envelope proteins and enzymes using mRNA. Instead, polyproteins, such as Gag protein(p55) and Gag-pol protein(p165), are processed by HIV protease into structural envelope proteins and functional enzymes e.g., reverse transcriptase and integrase, which are essential for virus replication. Inhibition of the protease activity would thus prevent virus replication, and indeed, previous studies have shown that viruses without functional proteases are incapable of inducing infection(Kohl et al., *Rroc. Nat. Acad. Sci.*, U.S.A., 85, 4686–4690(1988); and Peng et al., *J. Virol.*, 63, 2550(1989)). Accordingly, HIV protease inhibitors have been considered as a potential AIDS treating agent.

HIV protease consists of 99 amino acids and the structure was determined by X-ray crystallography(Navia et al., *Nature* 337, 615–620(1989); Wlodawer et al., *Science*, 245, 616–621(1989); and Miller et al., *Science*, 246, 1149–1152 (1989)).

HIV protease is present in a dimeric form; each monomer has a molecular weight of 10,793 daltons. HIV protease is classified as an aspartic protease since it is known to have the typical sequence of Asp-Thr-Gly at the active site.

In this connection, recent studies on HIV protease inhibitors have been focused on the development of compounds having a structure similar to the transition state of the enzyme with the expectation that they would have a high affinity to the protease (see Roberts et al., *Science*, 248, 358(1990); EP Publication Nos. 0337714, 0346847, 0356223, 0352000, 0357332, 0362002, 0361341; Bone et al., *J. Am. Chem. Soc.*, 113, 9382(1991)). Such compounds are, however, reversible inhibitors having limited activities. Irreversible inhibitors which can block the protease activity permanently would be more effective in treating AIDS.

The inventors have made efforts for the development of irreversible inhibitors by way of synthesizing and testing a new class of compounds having a cis-epoxide group which can bind permanently to the reaction site of HIV protease. (Korean Patent Application No. 93-10811).

SUMMARY OF THE INVENTION

Accordingly, it is a primary object of the present invention to provide novel compounds having improved inhibitory activity against HIV and a process for the preparation thereof.

Another object of the present invention is to provide compositions comprising the above compounds as active ingredients, useful for the prevention or treatment of AIDS or HIV infection.

In accordance with one aspect of the present invention, there is provided a novel cis-epoxide compound of formula (I) and the pharmacologically acceptable salts, hydrates and solvates thereof:

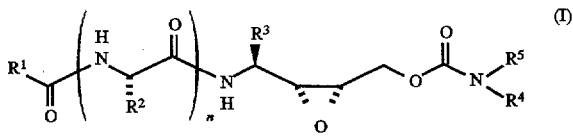

wherein:
$R^1$ is an aromatic group, a nitrogen-containing aromatic group, $C_{1-4}$ alkyl group optionally substituted with an aromatic group or a nitrogen-containing aromatic group, $C_{1-4}$ alkoxy group optionally substituted with an aromatic group or a nitrogen-containing aromatic group;

$R^2$ is an amino acid residue or a $C_{1-8}$ alkyl group substituted with a $C_{1-4}$ alkylsulfonyl group;

$R^3$ is a $C_{1-4}$ alkyl group optionally substituted with an aromatic group;

$R^4$ is hydrogen or a $C_{1-2}$ alkyl group;

$R^5$ is a $C_{1-10}$ alkyl group optionally substituted with an aromatic group; and n is 1 or 2.

DETAILED DESCRIPTION OF THE INVENTION

Referring to the novel cis-epoxide compound of formula (I) of this invention, the term "aromatic group" means a benzene or naphthalene radical carrying optional substituents and the term "nitrogen-containing aromatic group" refers to a pyridine or quinoline radical carrying optional substituents. It must also be understood that the compound of formula (I) may have a plurality of chiral carbons, and accordingly, the compound of the present invention is inclusive of all forms of possible stereoisomers, e.g., an optically pure single isomer, a racemic mixture, a diastereomeric mixture, etc.

In accordance with one embodiment of this invention, $R^1$ is preferably a phenyl, benzyl, quinolyl, quinolylmethyl, phenoxy, benzyloxy, quinolyloxy, quinolylmethoxy, phenoxymethyl or quinolyloxymethyl group; most preferably a quinolyl, benzyloxy or quinolyloxymethyl group;

$R^2$ is preferably a $C_{1-4}$ alkyl carrying an amido or sulfone functional group; most preferably an asparagine residue or a 2-methanesulfonyl-2-propyl group;

$R^3$ is preferably a $C_{1-2}$ alkyl substituted with a phenyl group carrying optional substituents; most preferably a benzyl group;

$R^4$ is preferably hydrogen, a methyl or ethyl group; most preferably hydrogen and;

$R^5$ is preferably a $C_{2-8}$ alkyl group optionally substituted with an aromatic group; most preferably a $C_{3-7}$ alkyl group optionally substituted with a phenyl group.

Representatives of desirable compounds according to the present invention are as follows:

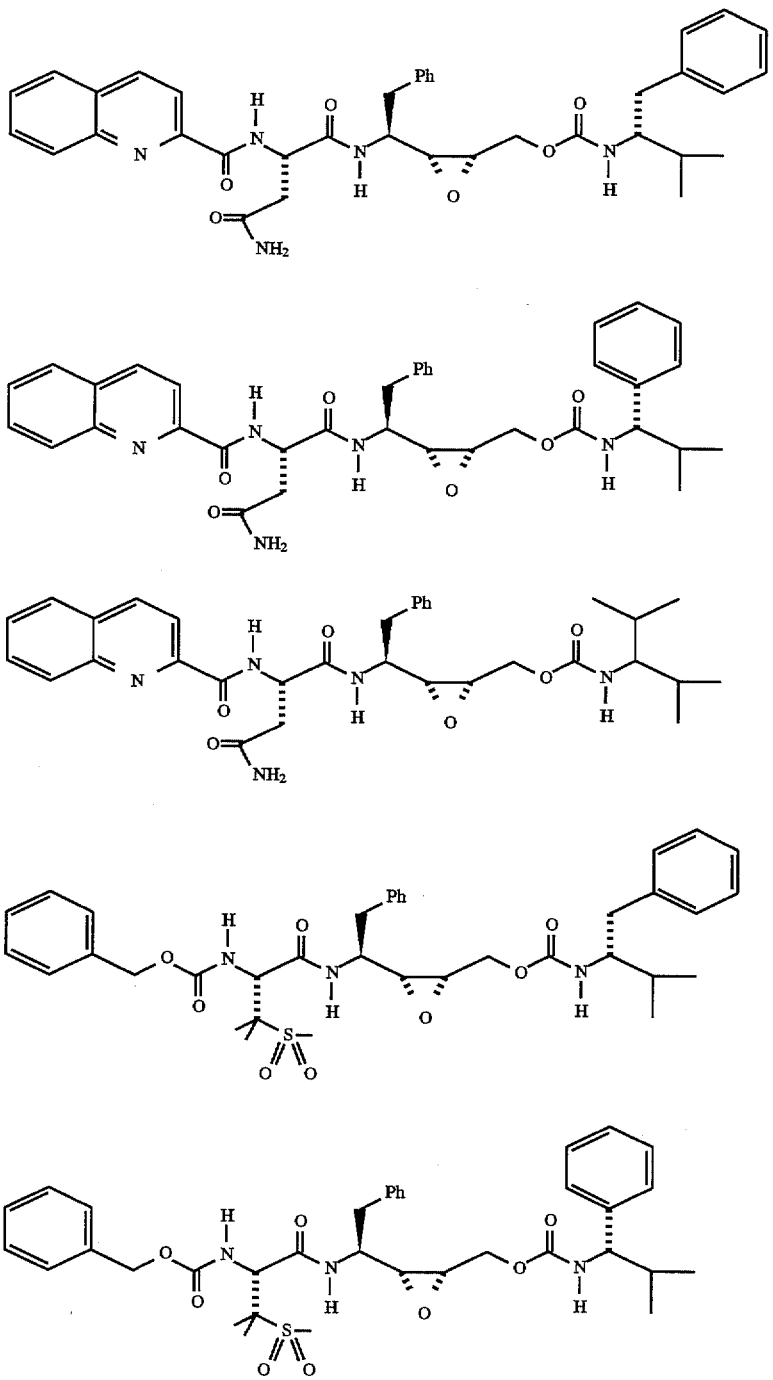

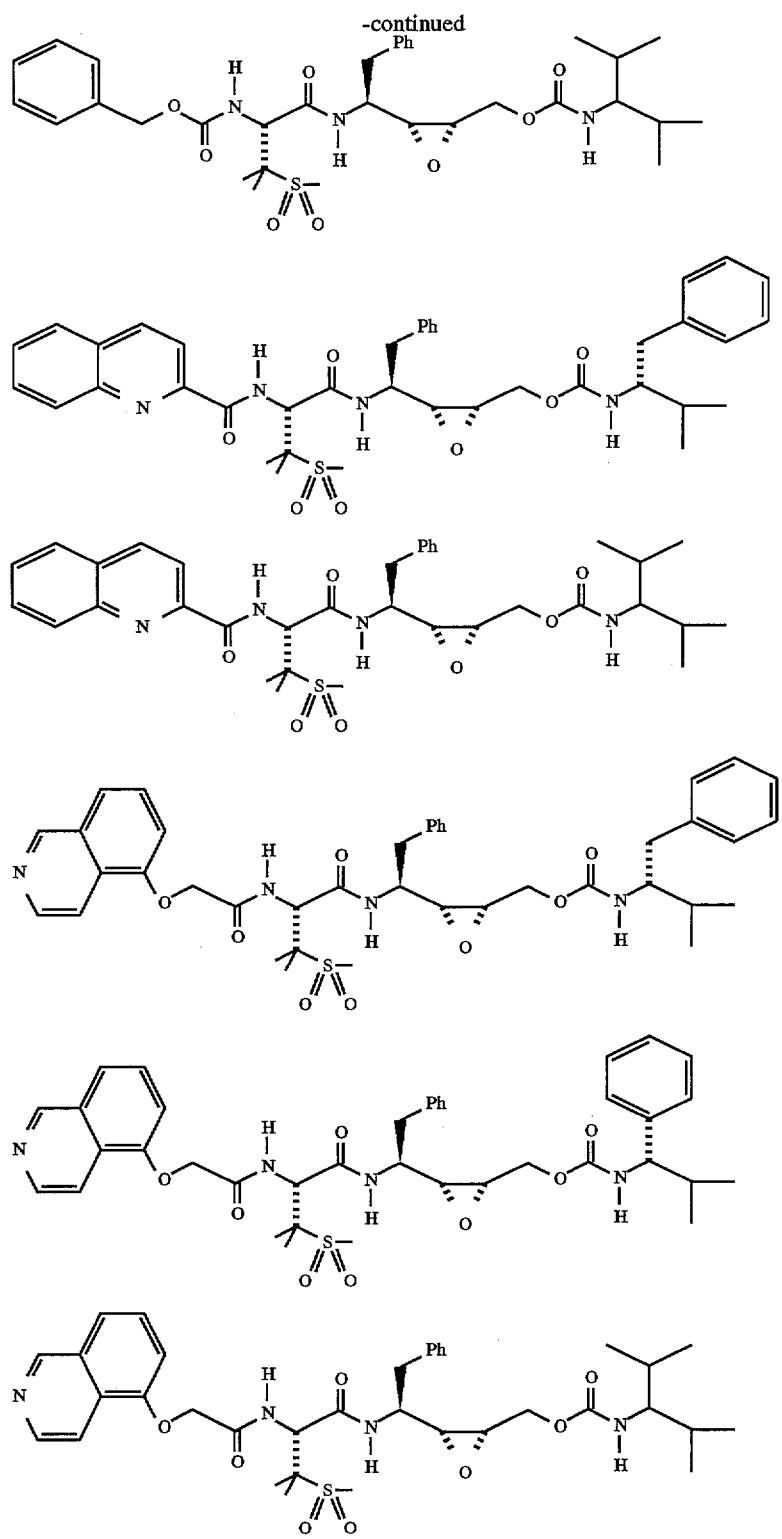
The compound of the formula (I) according to the present invention may be prepared as in Scheme 1.

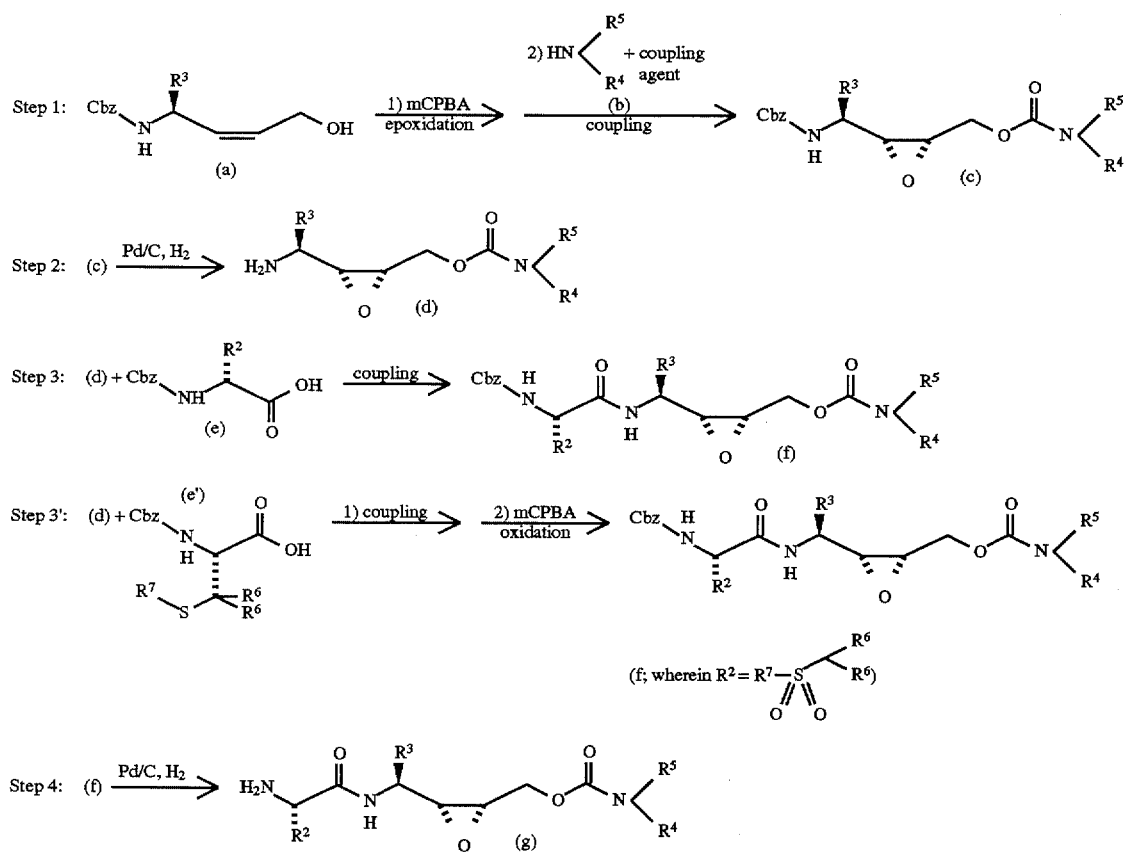

Step 5:

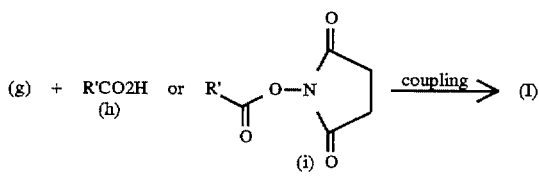

wherein
Cbz=benzyloxycarbonyl

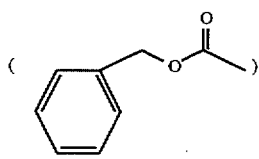

mCPBA=m-chloroperoxybenzoic acid
$R^6$: $C_{1-4}$ alkyl group
$R^7$: $C_{1-4}$ alkyl group In step 1 of Scheme 1, the compound of formula (a) is epoxidized with meta-chloroperoxybenzoic acid(mCPBA) and the epoxidized compound is coupled with the compound of formula (b) using a coupling agent to give the compound of formula (c). The benzyloxycarbonyl protecting group is removed from the compound of formula (c) to obtain the compound of formula (d) in step 2. In subsequent step 3, a coupling reaction between the compound of formula (d) and the compound of formula (e) is carried out. When $R^2$ is an alkyl group containing a sulfone group, step 3 may be substituted with step 3' wherein the compound of formula(e') is coupled with compound (d) and the resulting product is oxidized to obtain the compound of formula (f) having a sulfone group. The benzyloxycarbonyl protecting group of the compound of formula (f) is removed in step 4 to obtain the compound of formula (g). In step 5, a coupling reaction-between the compound of formula (g) and the compound of formula (h) or the compound of formula (i) is carried out to obtain the desired compound of formula (I).

In the above coupling reaction, coupling reagents may comprise, but not limited to, dicyclohexylcarbodiimide (DCC), 3-ethyl-3'-(dimethylamino)-propylcarbodiimide (EDC), bis-(2-oxo-3-oxazolidinyl)-phosphinic acid chloride (BOP-Cl), diphenylphosphorylazide (DPPA) and the like.

A carboxylic acid, e.g., the compound of formula (e) may be converted into an acid halide or an active ester derivative before carrying out a coupling reaction. Such acid halide derivatives include acid chloride, and suitable active ester derivatives are those commonly used to activate a carboxylic acid group for coupling with an amine to form an amide bond, or with an alcohol to form an ester bond: alkoxycarbonyl halides such as methoxycarbonyl chloride, isobutoxycarbonyl chloride, and the like; carboxylic acid anhydrides derived from coupling reagents; and, esters derived from N-hydroxy-benzotriazole, N-hydroxyphthalimide, N-hydroxysuccinimide, N-hydroxy-5-norbornene-2',3'-dicarboxamide and 2,4,5-trichlorophenol; and the like.

The removal of the benzyloxycarbonyl group may be carried out in accordance with a known method in the art, e.g., hydrogenolysis in the presence of a Pd/C catalyst under a $H_2$ pressure.

The compound of the formula (a) may also be prepared by a method illustrated in Scheme 2:

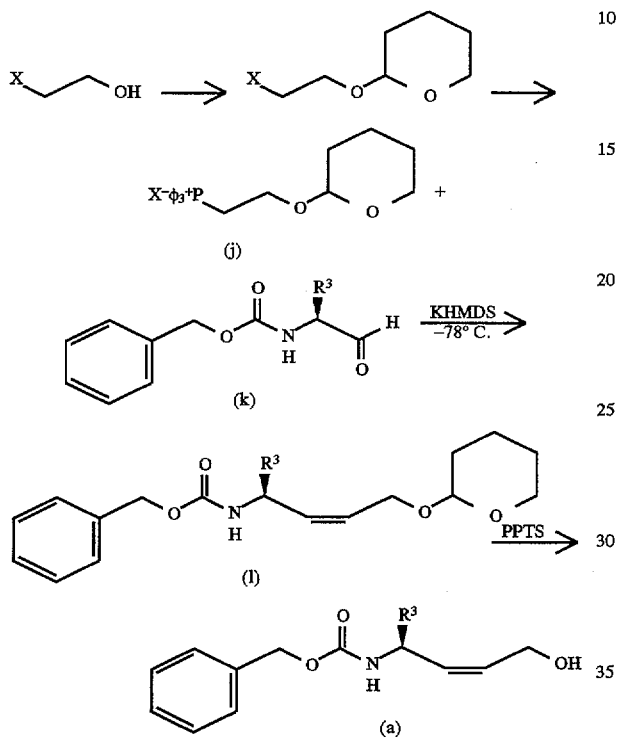

KHMDS: Potassium hexamethylenedisilazane
PPTS: Pyridium p-toluenesulfonate
X: Br or I Scheme 2 illustrates the process for preparing the cisene-allylic alcohol of the formula (a) by carrying out a Wittig reaction on the compound of formula (k) in accordance with the procedures disclosed in (Hiroshi et al., *J. Chem. Soc., Chem. Commu.*, 311–312(1987); and Adolphc Bohnstedt et al., *Tetrahedron Letters*, 34(33), 5217–5220(1993)).

The functionalized amine of formula (b) in the present invention may be prepared as illustrated in Schemes 3 and 4.

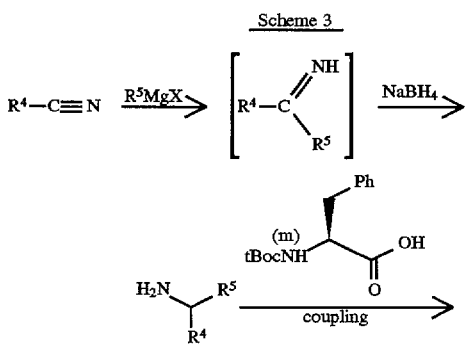

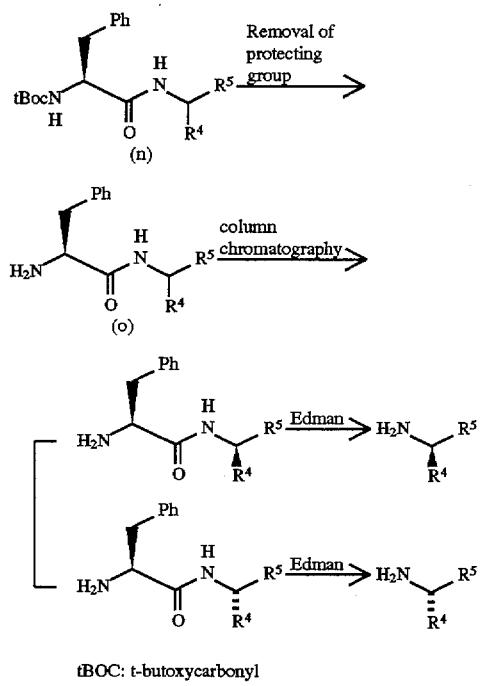

tBOC: t-butoxycarbonyl

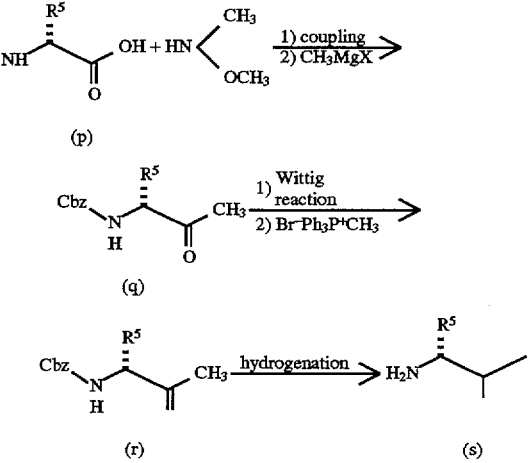

Cbz = benzyloxycarbonyl

In the above schemes, $R^4$, $R^5$ and X have same meaning as defined previously.

Scheme 3 shows a procedure for preparing the desired amine of formula (b) from a nitrile($R^4$CN) by conducting a Grignard reaction, following by a $NaBH_4$ reduction. The resulting amine is a racemic mixture, and therefore, it is coupled with N-t-butoxycarbonylphenylalanine, the t-butoxycarbonyl protecting group is removed and the resulting racemic mixture of the compound of formula (o) is separated into 2 diastereomers by column chromatography. Each of the diastereomers was finally converted to the corresponding optically pure amine by Edman's method.

Scheme 4 shows an alternative procedure for preparing an optically pure amine suitable for use in the present invention. Protected L- or D-amino acid of formula (p) is coupled with methoxymethyl amine, and then a Grignard reaction was conducted to obtain the compound of formula (q).

11

Subsequently, a Wittig reaction is carried out at −20° C. using potassium hexamethyldisilazane(KHMDS) to obtain the compound of formula (r), which is hydrogenated to obtain the amine of formula (s).

The compound of formula (e') used in step 3' of Scheme 1 may be prepared as illustrated in Scheme 5.

Scheme 5

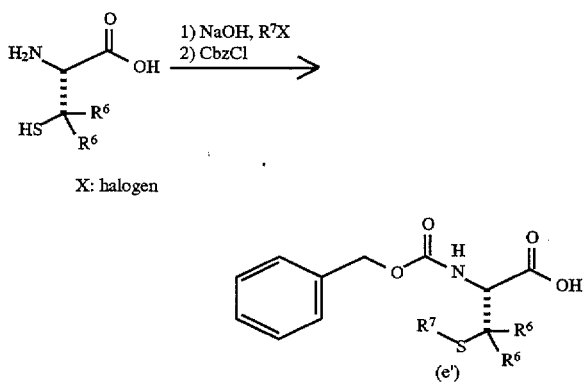

X: halogen

Scheme 5 illustrates a procedure involving the steps of alkylating the thiol group of a substituted cysteine under a basic condition,and introducing a benzyloxy protecting group to the amine function.

The compound of the present invention may be used for the prevention or treatment of AIDS or HIV infection because it has inhibitory activity against HIV protease. The total amount thereof which may be administered to a patient may range from 100 to 600 mg/kg of body weight every 24 hours for a period prescribed to treat the disease. The dosage may be adjusted based on all relevant factors, e.g., the patient's weight, age, sex, healthy condition, diet, excretion rate, mix of pharmacon; the kind and severity of the disease; the type of formulation; the compound used and the administration method thereof and others.

The compositions of the present invention may be administered orally or by injection. Suitable injection solutions, e.g., aqueous or oily suspensions for sterilized injections, may be prepared according to a conventional method by using suitable dispersing agents, hydrating agents or suspending agents. The solvents which may be used include polyethyleneglycol, ethyleneglycol, polypropyleneglycol, ethanol and the like.

Solid compositions for oral administration may be in the form of capsules, tablets, pills, powders and granules; the form of capsules is more preferred. In case of tablets, it is advantageous to produce them in the enteric-coated form. These compositions may include one or more inert diluents such as sucrose, lactose and starch, and a lubricant such as magnesium stearate.

The compounds of the present invention may be administered simultaneously with one or more other anti-AIDS agents or immunomodulators.

The compositions comprising the compounds of the present invention for the prevention and the treatment of HIV infection are not limited to those mentioned above, and other pharmaceutical composition containing the compounds of the present invention may be used for the prevention and the treatment of HIV infection.

The following Preparation Examples and Examples are provided for purposes of illustrating certain aspects of the present invention only; they are not to be construed as limiting the scope of the present invention in any way.

12

Preparation Example 1

Preparation of N-benzyloxycarbonyl-β-(S-methyl)-L-valine 8.9g (0.06mol) of β-mercapto-L-valine was added to a mixture of 120 ml of dioxane and 40 ml of water, cooled to 0° C. and then 20 ml of 6N NaOH aqueous solution was added. 9.24 g (0.066 mol) of methyl iodide was added to the resulting solution and the mixture was stirred for 3 hours at 0° C. and then 2 hours at room temperature to carry out the methylating reaction. The resulting methylated product was cooled to 0° C., and 15 ml of NaOH aqueous solution and 10.2 g (0.09 mol) of benzyl chloroformate were added slowly thereto. After stirring the mixture for 1 hour at 0° C. and 2 hours at 5° C., the reaction was terminated and the solvent was distilled off under a reduced pressure. In order to decompose residual benzyl chloroformate, a mixture of water and ether was added to the distillation residue, stirred and the organic layer was discarded. To the aqueous layer was added 60 ml of ethyl acetate and the mixture was adjusted to below pH 3 with 6N HCl. The organic layer was separated and dried over anhydrous $MgSO_4$, and the solvent was removed by distillation under a reduced pressure to obtain 14.25 g of the title compound(yield 80%).

$^1H$ NMR($CD_3OD$) δ1.2(s, 6H), 2.1(s, 3H), 4.3(d, 1H), 5.1(s, 2H), 7.1(m, 5H)

Preparation Example 2

2-1) Preparation of 2-methyl-3-R-benzyloxycarbonylamino-4-phenyl-1-butene 5.7 g (0.012 mol) of methyltriphenylphosphine bromide was dissolved in 40 ml of moisture-free toluene, and the resulting solution was cooled to −20° C. 22 ml (0.01 mol) of 0.5N potassium hexamethyldisilazane solution was added thereto slowly under a nitrogen atmosphere, and then, 2.63 g (0.01 mol) of R-3-benzyloxycarbonylamino-4-phenyl-2-butanone (synthesized by the method described by Nahm, Tetrahedron Letter, 54, 3815(1981)) was added thereto slowly. The resulting mixture was allowed to react for 30 minutes at −20° C., slowly warmed to room temperature and then stirred for 3 hours. After termination of the reaction, the solvent was removed by distillation under a reduced pressure and the residue was purified by column chromatography using ethyl acetate:hexane(10:90) as an eluent to obtain 2.2 g of the title compound(yield 84%).

$^1H$ NMR($CDCl_3$) δ1.77(s, 3H), 2.65–2.95(m, 2H), 4.27 (br, 1H), 4.51(b, 1H), 4.80(d, 2H), 5.15(s, 2H), 7.19–7.33(m, 10H)

2-2) Preparation of (R)-2-amino-3-methyl-1-phenylbutane 2.61 g(0.01 mol) of 2-methyl-3-R-benzyloxycarbonylamino-4-phenyl-1-butene was dissolved in 30 ml of methanol and 100 mg of 10% Pd/C was added thereto. The whole mixture was stirred for 3 hours under 1 atm of hydrogen atmosphere(rubber balloon). After removing the catalyst from the solution by passing through cellite, the solvent was removed to obtain 1.43 g of the title compound(yield 87%).

$^1H$ NMR($CDCl_3$) δ0.98(t, 6H), 1.65(m, 1H), 2.39(m, 1H), 2.82(m, 2H), 7.19–7.33(m, 5H)

Preparation Example 3

3-1) Preparation of 2-amino-3-methyl-1-phenylbutane hydrochloride

To 13.8 g (0.2 mol) of isobutyronitrile dissolved in 50 ml of anhydrous tetrahydrofuran(THF) was added 110 ml (0.22 mol) of 2.0M benzylmagnesiumchloride at room temperature, and the resulting mixture was refluxed for 1 hour and cooled to room temperature. Subsequently, 200 ml of methanol and 11.4 g (0.3 mol) of NaBH$_4$ were added thereto and stirred for 1 hour at room temperature. The resultant was adjusted to about pH 11 by adding 1N HCl. The above mixture was extracted with chloroform and dried over anhydrous Na$_2$SO$_4$, and methanolic HCl was added to obtain 37.5 g of the title compound(yield 94%).

$^1$H NMR(CDCl$_3$) δ1.08(m, 6H), 1.96(m, 1H), 2.90–3.16 (m, 2H), 3.37(m, 1H), 7.15–7.31(m, 5H), 8.36(b, 3H)

3-2) Preparation of N-[L-(N-t-butoxycarbonyl) phenylalanyl]-2-(1-phenyl-3-methylbutyl)amine To 26.5 g (0.1 mol) of N-t-butoxycarbonylphenylalanine was added 1.5 equivalent each of EDC and HOBT (hydroxybenzotriazole), and the resulting mixture was dissolved by adding 130 ml of DMF and 15 ml of triethylamine. To this solution, 20 g (0.1 mol) of the compound obtained in Preparation Example 3-1) was added at 0° C. and was stirred for 5 hours at room temperature. After removing the solvent by distillation under a reduced pressure, the residue was dissolved in ethyl acetate and washed successively with 1N HCl and with a saturated NaHCO$_3$ solution. The organic layer was dried over anhydrous MgSO$_4$ and the solvent was removed to obtain 37.7 g of the title compound(yield 92%).

3-3) Preparation of N-(L-phenylalanyl)-2-(1-phenyl-3-methylbutyl)amine 20.5 g (0.05 mol) of the compound-obtained in Preparation Example 3-2) was dissolved in a mixture of 30 ml of dichloromethane and 15 ml trifluoroacetic acid and the resulting solution was stirred for 1 hour at room temperature. The solvent was removed by distillation under a reduced pressure. And then column chromatography was conducted to separate two isomers using ethyl acetate as an eluent to obtain 8.0 g of an isomer having an Rf value of 0.50 as well as 7.4 g of the other isomer having an Rf value is 0.45. The total yield was 99%.

$^1$H NMR(CDCl$_3$) δ

1. Rf=0.50: 0.93(m, 6H), 1.80(m, 1H), 2.22(m, 1H), 2.63(m, 1H), 2.85(m, 1H), 3.05(m, 1H), 3.51(m, 1H), 4.11 (m, 1H), 7.10–7.34(m, 10H)

2. Rf=0.45: 0.91(m, 6H), 1.79(m, 1H), 2.65–2.70(m, 2H), 2.83(m, 1H), 3.18(m, 1H), 3.44(m, 1H), 4.08(m, 1H), 7.10–7.32(m,10H)

3-4) Preparation of 2-amino-3-methyl-1-phenylbutane 1.46 g (4.7 mmol) of each isomer obtained in Preparation Example 3-3) was dissolved in 50 ml of anhydrous dichloromethane. To the resulting solution was added 0.66 ml (5.5 mmol) of phenylisothiocyanate at room temperature, refluxed for 2 hours and cooled to room temperature. 10 ml of fluoroacetic acid was added thereto, followed by refluxing for 40 minutes at 60° C. After removing the solvent by distillation under a reduced pressure, the residue was dissolved in 20 ml of water, washed with ether, adjusted to about pH 11 by adding NaOH and extracted with chloroform to obtain each isomer of the title compound(yield 82–85%).

$^1$H NMR(CDCl$_3$) δ0.94(m, 6H), 1.11(bs, 2H), 1.65(m, 1H), 2.39(m, 1H), 2.82(m, 2H), 7.16–7.32(m, 5H)

[α]$_D$=1. -38.1 (c=0.12, dichloromethane) 2. +38.1 (c=0.12, dichloromethane)

Preparation Example 4

4-1) Preparation of 4S-(N-benzyloxycarbonyl)amino-5-phenyl-cis-2-pentene-1-yl 2-tetrahydropyranyl ether 5.64 g (12 mmol) of 2-(2-bromoethyloxy)tetrahydropyran triphenylphosphine salt was dissolved in 40 ml of tetrahydrofuran and stirred at -78° C. 25 ml of 0.5M potassium hexamethyldisilazane solution was added and the resulting mixture was maintained at -78° C. for 1 hour. Subsequently, 3.0 g (10.6 mmol) of L-(N–benzyloxycarbonyl) phenylalaninal dissolved in 15 ml of tetrahydrofuran(THF) was added to the above solution slowly at -78° C. The resulting mixture was stirred for 1 hour at -78° C. and then for 1 hour at room temperature. After stopping the reaction by adding water, the solvent was removed and the residue was dissolved in ethyl acetate. The resulting solution was washed successively with a saturated NaHCO$_3$ solution and with water, followed by drying the organic layer over anhydrous MgSO$_4$. Column chromatography was carried out to obtain 1.96 g of the title compound(yield 45%).

$^1$H NMR(CDCl$_3$) δ1.81(m, 6H), 3.01(m, 2H), 3.63(m, 1H), 4.21(m, 3H), 4.6–4.9(br, 3H), 5.13(s, 2H), 5.41(t, 1H), 5.62(m, 1H), 7.0–7.4(m, 10H)

4-2) Preparation of 4S-(N-benzyloxycarbonyl)amino-5-phenyl-cis-2-pentene-1-ol 2.47 g (6 mmol) of the compound obtained in Preparation Example 4-1) was dissolved in 80 ml of ethanol. 0.2 equivalent of pyridinium para-toluenesulfonate(PPTS) was added thereto and the resulting mixture was stirred for 24 hours at room temperature. Subsequently, the organic solvent was removed by distillation under a reduced pressure and the residue was dissolved in dichloromethane. The resulting solution was washed with a saturated NaHCO$_3$ solution and the organic layer was dried over anhydrous MgSO$_4$. Column chromatography was carried out to obtain 1.67 g of the title compound(yield 90%).

$^1$H NMR(CDCl$_3$) δ2.82(m, 2H), 3.41(m, 3H), 4.32(m, 1H), 4.83(br, 1H), 5.01(s, 2H), 5.21(t, 1H), 5.42(m, 1H), 7.0–7.4(m, 10H)

4-3) Preparation of 4S-(N-benzyloxycarbonyl)amino-5-phenyl-(3R, 2S)-epoxypentane-1-ol alcohol 311 mg (1 mmol) of the compound obtained in Preparation Example 4-2) was dissolved in 20 ml of dichloromethane. 3 equivalent of meta-chloroperoxybenzoic acid (mCPBA) was added thereto and the resulting mixture was stirred for 24 hours at room temperature. 30 ml of conc. Na$_2$S$_2$O$_3$ solution was added thereto and stirred for 30 minutes. The organic layer was washed with a saturated NaHCO$_3$ solution and dried over anhydrous MgSO$_4$. The organic solvent was removed to obtain 198 mg of the title compound(yield 63%).

$^1$H NMR(CDCl$_3$) δ2.8–3.2(m, 6H), 3.81(m, 1H), 4.83(br, 1H), 5.01(s, 2H), 7.0–7.4(m, 10H)

EXAMPLE 1

Preparation of 4S-[N-(2-quinolinecarbonyl)-L-asparaginyl]amino-(3R,2S)-epoxy-5-phenyl-pentyl N-2R-(1-phenyl-3-methylbutyl) carbamate 1-1) Preparation of 4S-(N-benzyloxycarbonylamino)-(3R,2S)-epoxy-5-phenyl-1-pentyl N-2R-(1-phenyl-3-methylbutyl) carbamate

[4S-[(N-benzyloxycarbonyl)amino]-(3R,2S)-epoxy-5-phenyl-1-pentoxy]succinimidylcarbonate was synthesized from 198 mg (0.6 mmol) of the compound obtained in Preparation Example 4—3) by the method disclosed in [Arunk. Ghosh et al., Tetrahedron Letter, 33, 2781–2784 (1992)]. 198 mg of the above compound was mixed with 122 mg (0.7 mmol) of the compound obtained in Preparation Example 2-2) and 3 equivalent of triethylamine and the mixture was dissolved in 30 ml of dichloromethane and stirred for 2 hours at room temperature. Subsequently, the resulting mixture was washed with a saturated NaHCO$_3$ solution and the organic layer was dried over anhydrous MgSO$_4$. The organic solvent was removed by distillation under a reduced pressure and column chromatography (hexane:ethyl acetate=3:7) was carried out to obtain 258 mg of the title compound(yield 81%).

hu 1H NMR(CDCl$_3$) δ0.81(dd, 6H), 2.02(m, 1H), 2.8–3.1 (m, 6H), 3.6–4.0(m, 4H), 4.9–5.3(m, 4H), 7.0–7.4(m, 15H)

1-2) Preparation of 4S-[N-(2-quinolinecarbonyl)-L-asparaginyl]amino-(3R,2S)-epoxy-5-phenyl-1-pentyl N-2R-(1-phenyl-3-methylbutyl) carbamate 258 mg (0.5 mmol) of the compound obtained in Example 1-1) was dissolved in 50 ml methanol, 25 mg of 10% Pd/C was added thereto and the whole mixture was stirred for 3 hours under 1 atm of hydrogen(rubber balloon). After removing the catalyst from the solution by passing through cellite, the solvent was removed by distillation under a reduced pressure. 173 mg (0.6mmol) of N-(2-quinolinecarbonyl)asparagine, each 1.5 equivalent of EDC and HOBT were dissolved in 10 ml of dimethylformamide and the amine obtained above was added thereto at 0° C. The resulting mixture was stirred for 6 hours at room temperature and the solvent was removed by distillation under a reduced pressure. The residue was dissolved in dichloromethane, washed with a saturated $NaHCO_3$ solution, and dried over anhydrous $Na_2SO_4$. The organic solvent was removed by distillation under a reduced pressure and column chromatography(hexane:ethyl acetate=3:7) was carried out to obtain 140 mg of the title compound(yield 43%).

$^1$H NMR($CDCl_3$) δ0.81(dd, 6H), 2.01(m, 1H), 2.6–3.0(m, 8H), 3.6–4.4(m, 5H), 5.02(m, 1H), 5.41(br, 1H), 6.43(br, 1H), 7.0–7.4(m, 10H), 7.5–8.3(m, 7H), 9.43(br, 1H)

FAB MS(M+1) 652

EXAMPLE 2 AND 3

A procedure similar to that described in Example 1 was used to prepare the compounds listed in Table 1.

EXAMPLE 4

Preparation of 4S-[(N-benzyloxycarbonyl)-β-methanesulfonyl-L-valinyl]amino-(3R,2S)-epoxy-5-phenyl-1-pentyl N-2R-(1-phenyl-3-methylbutyl) carbamate 258 mg (0.5 mmol) of the compound obtained in Example 1-1) was dissolved in 50 ml methanol, 25 mg of 10% Pd/C was added thereto and the mixture was stirred for 3 hours under 1 atm of hydrogen(rubber balloon). After removing the catalyst from the solution by passing through cellite, the solvent was removed by distillation under a reduced pressure. 148 mg (0.5 mmol) of the title compound of Preparation Example 1, 1.5 equivalent each of EDC, HOBT and triethylamine were dissolved in 50 ml of dimethylformamide and the amine obtained above was added thereto at 0° C. The resulting mixture was stirred for 3 hours at room temperature and the solvent was removed by distillation under a reduced pressure. The residue was dissolved in dichloromethane and washed with a saturated $NaHCO_3$ solution. The organic layer was dried over anhydrous $MgSO_4$ and 5 equivalent of meta-chloroperoxybenzoic acid (mCPBA) was added thereto. The resulting mixture was stirred for 2 hours, 10% $Na_2S_2O_3$ solution was added thereto and stirred for 30 minutes. The organic layer was washed with a saturated $NaHCO_3$ solution and dried over anhydrous $MgSO_4$. The residue was purified by column chromatography (hexane:ethyl acetate=3:7) to obtain 263 mg of the title compound(yield 76%).

$^1$H NMR($CDCl_3$) δ0.82(d, 6H), 1.4–2.0(m, 7H), 2.6–3.9 (m, 13H ), 4.63(br, 1H), 4.81(d, 1H), 5.0(s, 2H), 5.82(br, 1H), 7.0–7.5(m, 11H)

FAB MS(M+1) 694

EXAMPLE 5 AND 6

A procedure similar to that of Example 4 was used to prepare the compounds listed in Table 1.

EXAMPLE 7

Preparation of 4S-[N-2-quinolinecarbonyl-β-methanesulfonyl-L-valinyl]amino-(3R,2S)-epoxy-5-phenyl-1-pentyl N-2R-(1-phenyl-3-methylbutyl) carbamate 347 mg (0.5 mmol) of the compound obtained in Example 4 was dissolved in 20 ml methanol, 34 mg of 10% Pd/C was added thereto and the whole mixture was stirred for 3 hours under 1 atm of hydrogen(rubber balloon). After removing the catalyst from the solution by passing through cellite, the solvent was removed by distillation under a reduced pressure. 86.6 mg (0.5 mmol) of 2-quinolinecarboxylic acid and 1.5 equivalent each of EDC and HOBT were dissolved in 10 ml of dimethylformamide and the amine obtained above was added thereto at 0° C. The resulting mixture was stirred for 6 hours at room temperature and the solvent was removed by distillation under a reduced pressure. The residue was dissolved in dichloromethane and washed with a saturated $NaHCO_3$ solution. The organic layer was dried over anhydrous $MgSO_4$ and the organic solvent was removed by distillation under a reduced pressure. The residue was purified by column chromatography (hexane:ethyl acetate=3:7) to obtain 221 mg of the title compound(yield 62%).

$^1$H NMR($CDCl_3$) δ0.81(m, 6H), 1.4–2.0(m, 7H), 2.6–3.8 (m, 12H), 4.12(m, 2H), 4.63(br, 1H), 4.82(d, 1H), 5.42(br, 1H), 7.0–7.5(m, 10H), 9.33(br, 1H)

FAB MS(M+1) 715

EXAMPLE 8 AND 9

A similar procedure as in Example 7 was used to prepare the compounds listed in Table 1.

EXAMPLE 10

Preparation of 4S-[N-(5-isoquinolinyloxy methylenecarbonyl)-β-methanesulfonyl-L-valinyl] amino-(3R,2S )-epoxy-5-phenyl-1-pentyl N-2R-(1-phenyl-3-methylbutyl) carbamate 347 mg (0.5 mmol) of the compound obtained in Example 4 was dissolved in 20 ml methanol, 34 mg of 10% Pd/C was added thereto and the mixture was stirred for 3 hours under 1 atm of hydrogen(rubber balloon). After removing the catalyst from the solution by passing through cellite, the solvent was removed by distillation under a reduced pressure. 101 mg (0.5 mmol) of 5-isoquinolinyloxy acetic acid and 1.5 equivalent each of EDC and HOBT were dissolved in 10 ml of dimethylformamide and the above obtained amine was added thereto at 0° C. The resulting mixture was stirred for 6 hours at room temperature and the solvent was removed by distillation under a reduced pressure. The residue was dissolved in dichloromethane and washed with a saturated $NaHCO_3$ solution. The organic layer was dried over anhydrous $Na_2SO_4$ and the organic solvent was removed by distillation under a reduced pressure. The residue was purified by column chromatography (hexane:ethyl acetate=3:7) to obtain 316 mg of the title compound(yield 85%).

$^1$H NMR($CDCl_3$) δ0.83(m, 6H), 1.5–2.0(m, 7H), 2.4–3.8 (m, 12H), 4.13(m, 1H), 4.63(br, 1H), 4.71(s, 2H), 4.82(d, 1H), 5.82(br, 1H), 7.0–8.5(m, 16H), 9.32(br, 1H)

FAB MS(M+1) 745

EXAMPLE 11 AND 12

A procedure similar to that of Example 10 was used to obtain the compounds listed in Table 1.

TABLE 1

| Ex. No. | Compound | FAB MS (M+1) | ¹H NMR(CDCl₃)δ |
|---|---|---|---|
| 1 | | 652 | 0.81(d, d, 6H), 2.01(m, 1H), 2.6~3.0(m, 8H), 3.6~4.4(m, 5H), 5.02(m, 1H), 5.41(br, 2H), 6.43(br, 1H), 7.0~7.4(m, 10H), 7.5~8.3(m, 7H), 9.43(br, 1H) |
| 2 | | 638 | 0.81(d, d, 6H), 2.01(m, 1H), 2.6~3.0(m, 6H), 3.6~4.4(m, 4H), 4.42(m, 1H), 5.0(m, 1H), 5.41(br, 2H), 6.41(br, 1H), 7.0~7.4(m, 10H), 7.5~8.3(m, 7H), 9.42(br, 1H) |
| 3 | | 604 | 0.81(d, d, 12H), 1.81(m, 2H), 2.8~3.2(m, 7H), 3.83(m, 2H), 4.11(m, 1H), 4.82(br, 1H), 5.01(m, 1H), 5.81(br, 1H), 6.62(br, 1H), 7.0~7.3(m, 5H), 7.6~8.3(m, 7H), 9.41(br, 1H) |
| 4 | | 694 | 0.82(d, d, 6H), 1.4~2.0(m, 7H), 2.6~3.9(m, 3H), 4.63(br, 1H), 4.81(d, 1H), 5.0(s, 2H), 5.6(br, 1H), 7.0~7.5(m, 15H) |
| 5 | | 680 | 0.81(m, 6H), 1.4~2.0(m, 7H), 2.6~3.9(m, 10H), 4.22(m, 1H), 4.61(br, 1H), 4.8~5.1(m, 4H), 5.63(br, 1H), 7.0~7.4(m, 10H) |
| 6 | | 646 | 0.92(m, 12H), 1.4~2.1(m, 8H), 2.6~3.8(m, 11H), 4.61(br, 1H), 4.8~5.1(m, 4H), 5.62(br, 1H), 7.0~7.4(m, 10H) |

TABLE 1-continued

| Ex. No. | Compound | FAB MS (M+1) | ¹H NMR(CDCl₃)δ |
|---|---|---|---|
| 7 | | 715 | 0.81(m, 6H), 1.4~2.0(m, 7H), 2.6~3.8(m, 12H), 4.12(m, 1H), 4.63(br, 1H), 4.82(d, 1H), 5.42(br, 1H), 7.0~7.5(m, 10H), 7.6~8.2(m, 6H), 9.33(br, 1H) |
| 8 | | 701 | 0.82(m, 6H), 1.4~2.0(m, 7H), 2.6~3.8(m, 10H), 4.31(m, 1H), 4.72(br, 1H), 5.03(d, 1H), 5.61(br, 1H), 7.0~7.5(m, 10H), 7.6~8.3(m, 6H), 9.42(br, 1H) |
| 9 | | 667 | 0.91(m, 12H), 1.4~2.1(m, 8H), 2.6~3.8(m, 10H), 4.62(br, 1H), 5.02(d, 1H), 5.63(br, 1H), 5.61(br, 1H), 7.1~7.4(m, 5H), 7.5~8.2(m, 6H), 9.42(br, 1H) |
| 10 | | 745 | 0.83(m, 6H), 1.5~2.0(m, 7H), 2.4~3.8(m, 12H), 4.13(m, 1H), 4.63(br, 1H), 4.71(s, 2H), 4.82(d, 1H), 5.82(br, 1H), 7.0~8.5(m, 16H), 9.32(br, 1H) |
| 11 | | 731 | 0.82(m, 6H), 1.5~2.0(m, 7H), 2.4~3.8(m, 9H), 4.11(m, 1H), 4.32(m, 1H), 4.65(br, 1H), 4.73(s, 2H), 4.94(d, 1H), 5.81(br, 1H), 7.0~8.5(m, 16H), 9.22(br, 1H) |

TABLE 1-continued

| Ex. No. | Compound | FAB MS (M+1) | $^1$H NMR(CDCl$_3$)δ |
|---|---|---|---|
| 12 | 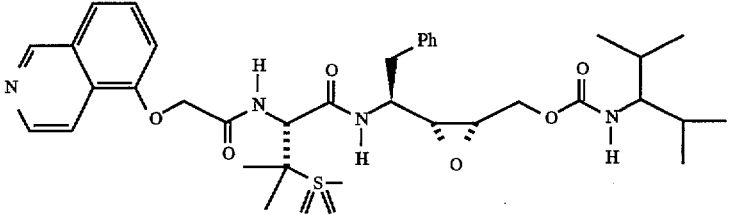 | 697 | 0.81(m, 12H), 1.5~2.0(m, 8H), 2.6~3.8(m, 11H), 4.61(br, 1H), 4.72(s, 2H), 5.11(d, 1H), 5.7(br, 1H), 7.0~8.4(m, 11H), 9.42(br, 1H) |

Assay for inhibitory effect on HIV protease

The inhibitory effect on HIV protease of the compounds of the present invention was determined by the following method.

To a buffer solution comprising 50 mM sodium acetate, pH 0.5, 1 mM dithiothreitol(DTT), 1 mM ethylenediamine-tetra-acetate (EDTA), 0.75M ammonium sulfate and 0.1% NP 40(NONIGET P-40; Sigma Chemical Co., U.S.A.) was added a measured amount of a compound selected from Compound Nos. 1 to 12 to prepare a preincubation solution. Inhibition reaction was started with the addition of 2.6 nM of HIV-1 protease to the preincubation solution. Each of 10 μl sample of the reaction solution taken at a given time interval was added to 80 μl of assay solution containing 100 μl of reaction substrate in the same buffer solution as above to assay for the residual enzyme activity. In this context, an oligopeptide consisting of 11 amino acids, i.e., H-His-Lys-Ala-Arg-Val-Leu-Phe-(p-NO$_2$)-(Glu-Ala-Ile-Ser-NH$_2$), was used as a reaction substrate, which oligopeptide was to be cleaved in two by the breakage of amide bond between Leu and Phe-(P-NO$_2$) upon the attack of HIV protease. The reaction rate was determined by subjecting the substrate before the reaction and the product after the reaction to HPLC separation and then measuring the relative amount of the product, using the strong absorbance of (p NO$_2$)-Phe at 280 nm. The amounts of reduction in enzyme activity according to the elapsed time were measured and the natural logarithmic values(1 n) of the measured amounts were plotted against time to obtain a linear graph and $k_{obs}$ was calculated from the slope of the linear graph.

The inhibition constant was calculated according to the following equation:

$$\frac{1}{k_{obs}} = \frac{1}{k_{ina}} + \frac{K_1}{k_{ina}} \cdot \frac{1}{[I]}$$

wherein:

$k_{obs}$ is a rate constant indicating the rate of reduction in enzyme activity according to the elapsed time under the presence of a given concentration of inhibitor, $K_{ina}$ is a rate constant indicating the rate of chemical reaction forming covalent bond between an enzyme and an inhibitor in Michaelis-Menten complex, $K_I$ is an inhibition constant indicating the dissociation rate of Michaelis-Menten complex into an enzyme and an inhibitor, and

[I] means the inhibitor concentration.

The above equation is applicable to an experiment carried out under the condition in which the concentration of inhibitor is far higher than that of enzyme (Steady State Kinetic). In case that the experiment was carried out under the condition in which the concentrations of inhibitor and enzyme were about the same, because of the superior inhibition effect of the inhibitor, the mechanism equation of E+I⇌EI→EI'(wherein, E means an enzyme, I means an inhibitor, EI means a Michaelis-Menten complex and EI' means a complex having covalent bond formed between an enzyme and an inhibitor; and $K_1$ and $k_{ina}$ have the same meanings as defined above) was used to calculate the relative concentration of active enzyme, i.e., [E]/([E]+[EI]+[EI']) in every given time. The inhibition constants $K_I$ and $k_{ina}$ and second order rate constant $k_{ina}/K_I$ were obtained by inputting the value of [E]/([E]+[EI]+[EI']) into KINSIM/FITSIM program. In case that second order rate constant $k_{ina}/K_I$ is larger than $10^9$, it is hard to calculate the exact values by KINSIM/FITSIM program [Williams, J. W. and Morrison, J. F., Methods, Enzymol., 63, 437-466 (1079); and Zimmerle, C. T. and Frieden, C., J. Biochem., 258, 381-387(1989)]. The inhibition constants thus obtained are listed in Table 2.

The results in Table 2 show that each of the compounds of the present invention has a large second order rate constant $k_{ina}/K_I$, which fully demonstrates that an essentially irreversible reaction takes place between HIV protease and the compound of this invention.

Determination of anti-viral activity and cytotoxicity

The anti-viral activity of the compounds of the present invention was determined by measuring the concentration of he compounds that inhibits the proliferation of HIV by 50%(IC$_{50}$) through a survey for syncytium formation or reverse transcriptase assay.

1×10$^5$ cells of each of H9(ATCC HTB 176) and Sup T1 cell lines were added to the wells of a 24-well microtiter plate and various concentrations of the compounds of the present invention were added thereto. 200 TCID$_{50}$(200-fold of 50% tissue culture infection dose) of HIV-1 inoculum and rpmi-1640 medium(Sigma Chemical Co., U.S.A) were added successively to the wells and the plate was incubated at 37° C. In case of Sup T1, the number of syncytium formed was investigated after 3 to 9 days. IC$_{50}$ of each compound was determined by measuring the concentration of inhibitor that can reduce the number of syncytium by 50% compared with those formed in the same condition without the inhibitor.

In case of H9, three-quarters(¾) of the culture medium in volume was refreshed every 3 days; and after 9 days, 6 ml of the culture fluid was taken and 2.5 ml of 30% polyethyleneglycol(PEG, M. W. 6000–8000) and 0.4M NaCl were added thereto. The resulting solution was allowed to stand at 0° C. overnight to precipitate virus particles. The solution was centrifuged at 2000 rpm for 45 minutes, the supernatant was discarded therefrom and the precipitate was diluted with 20 µl of a reverse transcriptase suspension buffer(50 mM tris-HCl, pH 7.5, 1 mM dithiothreitol, 20% glycerol, 0.25M KCl and 0.25% Triton X-100). The resulting suspension was stored in an Effendorf tube at −70° C. until used. A procedure of freezing said virus suspension for 2 minutes in dry ice and thawing same at 37° C. for 2 minutes was repeated three times and the resulting suspension was centrifuged at 4° C. The resulting supernatant was used in carrying out the reverse transcriptase assay.

10 µl of the said viral suspension was added to a solution of: 10 µl of buffer solution(250 mM tris-HCl, pH 7.5, 37.5 mM $MgCl_2$, 0.25% triton X-100), 1.2 µl of 200 mM dithiothreitol, 5 µl of 100 µM oligo(dT)-poly(A)(Boeringer Manheim, 12–18 oligomer), 1 µl(1 µCi) of $^3$H-TTP (Thymidinetri-phosphate) and 23.6 µl of water; and the resulting mixture was placed at 37° C. After 1 hour, the mixture was poured onto a WHATMAN DEB1 filter and the filter was washed three times with 5 ml of 2× SSC buffer solution(17.53 g of sodium chloride, 8.82 g of sodium citrate, pH 7.0, 1 liter of water) for about 10 minutes each time and twice with 95% methanol for 10 seconds. The filter was put onto aluminum foil and dried with an infra-red lamp. The amount of radioactivity was counted using a liquid scintillation counter.

To determine the cytotoxicity of the compounds of the present invention, 0.1 µM to 100 µM of the novel compounds were added to H9 cell or Sup T1 cell and the mixture was cultured on a rpmi-1640 medium at 37° C. The medium was refreshed every 3 days and the extent of cell proliferation was observed using Hemacytometer according to the trypan blue dye exclusion technique which is well known in the art. $CT_{50}$(i.e., concentration that causes death of cells by 50%) was determined. TABLE 2 shows the anti-viral activities($IC_{50}$) and cytotoxicities ($CT_{50}$) of the tested compounds of the present invention.

TABLE 2

| Ex. No. | $k_{in}/K_I$ (min$^{-1}$M$^{-1}$) | $IC_{50}$(ηM) | $CT_{50}$ (µM) |
|---|---|---|---|
| 1 | $10^9$–$10^{10}$ | 125 | >10 |
| 2 | $10^9$–$10^{10}$ | 130 | >10 |
| 3 | $10^9$–$10^{10}$ | 110 | >10 |
| 4 | $10^9$–$10^{10}$ | 15 | >10 |
| 5 | $10^9$–$10^{10}$ | 50 | >10 |
| 6 | $10^9$–$10^{10}$ | 50 | >10 |
| 7 | $10^9$–$10^{10}$ | 20 | >10 |
| 8 | $10^9$–$10^{10}$ | 100 | >10 |
| 9 | $10^9$–$10^{10}$ | 80 | >10 |
| 10 | $10^9$–$10^{10}$ | 12 | >10 |
| 11 | $10^9$–$10^{10}$ | 15 | >10 |
| 12 | $10^9$–$10^{10}$ | 50 | >10 |

As can be seen from the above results, the compound of the formula (I) of the present invention are irreversible HIV protease inhibitors having a high inhibitory effect and low cytotoxicity, and therefore, useful in the prevention or treatment of AIDS or HIV infection.

What is claimed is:

1. A cis-epoxide compound of formula (I) and pharmaceutically acceptable salts, hydrates and solvates thereof:

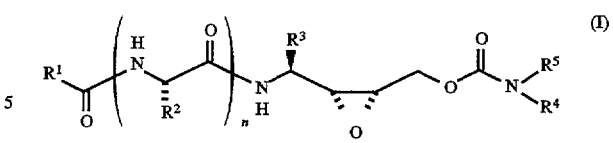

wherein:

$R^1$ is an aromatic group, a nitrogen-containing aromatic group, $C_{1-4}$ alkyl group optionally substituted with an aromatic group or a nitrogen-containing aromatic group, $C_{1-4}$ alkoxy group optionally substituted with an aromatic group or a nitrogen-containing aromatic group;

$R^2$ is an amino acid residue or a $C_{1-8}$ alkyl group substituted with a $C_{1-4}$ alkylsulfonyl group;

$R^3$ is a $C_{1-4}$ alkyl group optionally substituted with an aromatic group;

$R^4$ is hydrogen or a $C_{1-2}$ alkyl group;

$R^5$ is a $C_{1-10}$ alkyl group optionally substituted with an aromatic group; and n is 1 or 2.

2. The cis-epoxide compound of claim 1, wherein $R^3$ is a benzyl group, $R^4$ is hydrogen and n is 1.

3. The cis-epoxide compound of claim 2, wherein $R^1$ is a quinoline radical, a benzyloxy group or a 5-isoquinolinyloxy methyl group.

4. The cis-epoxide compound of claim 2, wherein 2 is an asparagine residue or a 2-methanesulfonyl-2-propyl substituent.

5. The cis-epoxide compound of claim 2, wherein $R^5$ is a 2,4-dimethyl-2-pentyl group, a 1-phenyl-3-methyl-2-butyl group or a 1-phenyl-2-methyl-1-propyl group.

6. The cis-epoxide compound of claim 1, which is selected from the group consisting of:

4S-[N-(2-quinolinecarbonyl)-L-asparaginyl]amino-(3R,2S)-epoxy-5-phenyl-1-pentyl N-2R-(1-phenyl-3-methylbutyl)carbamate;

4S-[N-(2-quinolinecarbonyl)-L-asparaginyl]amino-(3R,2S)-epoxy-5-phenyl-1-pentyl N-1S-(1-phenyl-2-methylpropyl)carbamate;

4S-[N-(2-quinolinecarbonyl)-L-asparaginyl]amino-(3R,2S)-epoxy-5-phenyl-1-pentyl N-3-(2,4-dimethylpentyl) carbamate;

4S-[N-(2-benzyloxycarbonyl)-β-methanesulfonyl-L-valinyl]amino-(3R,2S)-epoxy-5-phenyl-1-pentyl N-2R-(1-phenyl-3-methylbutyl) carbamate;

4S-[N-(2-benzyloxycarbonyl)-β-methanesulfonyl-L-valinyl]amino-(3R,2S)-epoxy-5-phenyl-1-pentyl N-1S-(1-phenyl-2-methylpropyl) carbamate;

4S-[N-(2-benzyloxycarbonyl)-β-methanesulfonyl-L-valinyl]amino-(3R,2S)-epoxy-5-phenyl-1-pentyl N-3-(2,4-dimethylpentyl) carbamate;

4S-[N-(2-quinolinecarbonyl)-β-methanesulfonyl-L-valinyl]amino-(3R,2S)-epoxy-5-phenyl-1-pentyl N-2R-(1-phenyl-3-methylbutyl) carbamate;

4S-[N-(2-quinolinecarbonyl)-β-methanesulfonyl-L-valinyl]amino-(3R,2S)-epoxy-5-phenyl-1-pentyl N-1S-(1-phenyl-2-methylpropyl) carbamate;

4S-[N-(2-quinolinecarbonyl)-β-methanesulfonyl-L-valinyl]amino-(3R,2S)-epoxy-5-phenyl-1-pentyl N-3-(2,4-dimethylpentyl) carbamate;

4S-[N-(5-isoquinolinyloxymethylenecarbonyl)-β-methanesulfonyl-L-valinyl]amino-(3R,2S)-epoxy-5-phenyl-1-pentyl N-2R-(1-phenyl- 3-methylbutyl) carbamate;

4S-[N-(5-isoquinolinyloxymethylenecarbonyl)-β-methanesulfonyl-L-valinyl]amino-(3R,2S)-epoxy-5- phenyl-1-pentyl N-1S-(1-phenyl-2-methylpropyl) carbamate; and

4S-[N-(5-isoquinolinyloxymethylenecarbonyl)-β-methanesulfonyl-L-valinyl]amino-(3R,2S)-epoxy-5-phenyl-1-pentyl N-3-(2,4-dimethylpentyl)carbamate.

7. A pharmaceutical composition comprising a therapeutically effective amount of the cis-epoxide compound of claims 1 to 6, pharmaceutically acceptable salts, hydrates or solvates thereof, and a pharmaceutically acceptable carrier.

8. A process for the preparation of the compound of formula (I) of claim 1 comprising the steps of:

- epoxidizing the compound of formula (a) to obtain an epoxidized compound and coupling the epoxidized compound with the compound of formula (b) to obtain the compound of formula (c);
- removing the benzyloxycarbonyl protecting group from the compound of formula (c) to obtain the compound of formula (d);
- preparing the compound of formula (f) either by coupling the compound of formula (d) and the compound of formula (e); or by coupling the compound of formula (d) and the compound of formula (e') and oxidizing the coupled product;
- removing the benzyloxycarbonyl protecting group from the compound of formula (f) to obtain the compound of formula (g); and
- coupling the compound of formula (g) with the compound of formula (h) or with the compound of formula (i) to obtain the desired compound of formula (I):

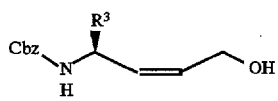  (a)

  (b)

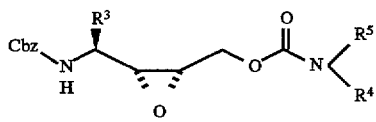  (c)

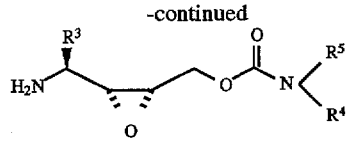  (d)

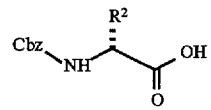  (e)

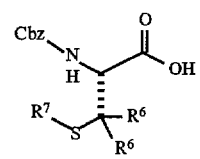  (e')

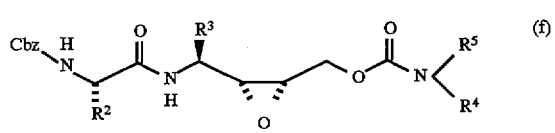  (f)

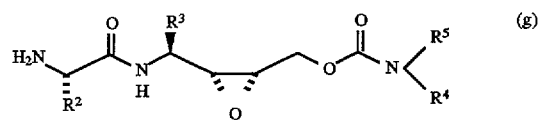  (g)

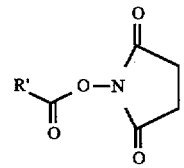 R'CO2H  (h)

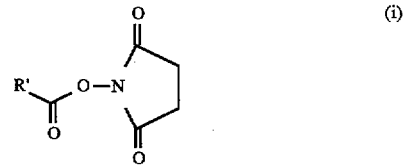  (i)

(wherein:

$R^2$, $R^3$, $R^4$ and $R^5$ have the same meanings as defined in claim 1;

$R^6$ and $R^7$ are independently $C_{1-4}$ alkyl group; and Cbz is a benzyloxycarbonyl group).

* * * * *